(12) United States Patent
Leonard et al.

(10) Patent No.: US 8,540,976 B2
(45) Date of Patent: Sep. 24, 2013

(54) POLY (NON-CONJUGATED DIENE) BASED SUNSCREENS

(75) Inventors: James Klein Leonard, Madison, WI (US); Kenneth Berry Sloan, Gainesville, FL (US); Kenneth Boone Wagener, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 13/257,775

(22) PCT Filed: Apr. 1, 2010

(86) PCT No.: PCT/US2010/029646
§ 371 (c)(1),
(2), (4) Date: Sep. 20, 2011

(87) PCT Pub. No.: WO2010/115009
PCT Pub. Date: Oct. 7, 2010

(65) Prior Publication Data
US 2012/0009133 A1    Jan. 12, 2012

Related U.S. Application Data

(60) Provisional application No. 61/165,764, filed on Apr. 1, 2009.

(51) Int. Cl.
*A61K 31/00*    (2006.01)
(52) U.S. Cl.
USPC .................. 424/78.06; 424/401; 424/78.02
(58) Field of Classification Search
None
See application file for complete search history.

(56) References Cited

U.S. PATENT DOCUMENTS

| | | | |
|---|---|---|---|
| 3,864,473 A | 2/1975 | Ciaudelli | |
| 4,004,074 A | 1/1977 | Gerecht et al. | |
| 4,233,430 A | 11/1980 | Jacquet et al. | |
| 4,524,061 A | 6/1985 | Cho et al. | |
| 4,999,186 A * | 3/1991 | Sabatelli et al. | 424/60 |
| 5,099,027 A | 3/1992 | Vogl et al. | |
| 5,134,223 A | 7/1992 | Langer et al. | |
| 5,243,021 A | 9/1993 | Langer et al. | |
| 5,250,652 A | 10/1993 | Langer et al. | |
| 5,487,885 A | 1/1996 | Sovak et al. | |
| 5,519,101 A | 5/1996 | Nubel et al. | |
| 5,607,664 A | 3/1997 | Ascione et al. | |
| 5,741,924 A | 4/1998 | Sovak et al. | |
| 5,753,209 A | 5/1998 | Ascione et al. | |
| 5,888,481 A | 3/1999 | Horn et al. | |
| 5,993,789 A | 11/1999 | Bonda et al. | |

(Continued)

OTHER PUBLICATIONS

Akcelrud, Leni, Electroluminescent polymers, Progress in Polymer Science, 28 (2003) 897-962.*

(Continued)

*Primary Examiner* — Anand Desai
*Assistant Examiner* — Melissa Mercier
(74) *Attorney, Agent, or Firm* — Saliwanchik, Lloyd & Eisenschenk

(57) ABSTRACT

A poly(non-conjugated diene) based sunscreen has a plurality of repeating units where each repeating unit has at least one UV absorbing chromophore that is situated between and connected by chains to two mono-ene units where each UV absorbing chromophore absorb UVA and UVB light. The poly(non-conjugated diene) based sunscreen can be included with a vehicle for application to the skin to prevent sunburn. The poly(non-conjugated diene) based sunscreen can be prepared by acyclic diene metathesis polymerization.

17 Claims, 5 Drawing Sheets

(56) References Cited

U.S. PATENT DOCUMENTS

| | | | |
|---|---|---|---|
| 6,159,456 | A | 12/2000 | Candau |
| 6,200,557 | B1 | 3/2001 | Ratcliff |
| 6,214,324 | B1 | 4/2001 | Candau |
| 6,221,343 | B1 | 4/2001 | Richard et al. |
| 6,251,373 | B1 | 6/2001 | Candau |
| 6,312,673 | B2 | 11/2001 | Richard et al. |
| 6,376,679 | B2 | 4/2002 | Leduc et al. |
| 6,800,274 | B2 | 10/2004 | Bonda et al. |
| 6,890,521 | B2 | 5/2005 | Bonda |
| 6,899,866 | B2 | 5/2005 | Bonda |
| 6,919,473 | B2 | 7/2005 | Bonda et al. |
| 6,926,887 | B2 | 8/2005 | Bonda et al. |
| 6,962,692 | B2 | 11/2005 | Bonda et al. |
| 7,087,692 | B2 | 8/2006 | Koshti et al. |
| 7,291,322 | B2 | 11/2007 | Candau |
| 2001/0026789 | A1 | 10/2001 | Richard et al. |
| 2002/0054860 | A1 | 5/2002 | Candau |
| 2004/0101498 | A1 | 5/2004 | Koshti et al. |
| 2004/0213746 | A1 | 10/2004 | Candau |
| 2005/0136012 | A1 | 6/2005 | Gonzalez et al. |
| 2005/0186152 | A1 | 8/2005 | Bonda et al. |
| 2005/0191249 | A1 | 9/2005 | Bonda et al. |
| 2006/0233729 | A1 | 10/2006 | Rose et al. |
| 2007/0020204 | A1 | 1/2007 | Candau |

OTHER PUBLICATIONS

Department of Health and Human Services, Food and Drug Administration "Sunscreen Drug Products for Over-The-Counter Human Use; Final Monograph" Federal Register, Rules and Regulations, May 21, 1999, 64(98):27666-27693.

* cited by examiner

… (US 8,540,976 B2)

POLY (NON-CONJUGATED DIENE) BASED SUNSCREENS

CROSS-REFERENCE TO RELATED APPLICATIONS

This application is the U.S. national stage application of International Patent Application No. PCT/US2010/029646, filed Apr. 1, 2010, which claims the benefit of U.S. Provisional Application Ser. No. 61/165,764, filed Apr. 1, 2009, the disclosures of which are hereby incorporated by reference in their entireties, including all figures, tables and drawings.

The subject invention was made with government support under a research project supported by National Science Foundation Private Investigator Grant, Contract No. DMR-0703261 and 0314110. The government has certain rights to this invention.

BACKGROUND OF INVENTION

UV radiation penetrates the ozone layer over two wavelength regimes, UVB (290-320 nm) and UVA (320-400 nm). UVB acts directly on biological molecules, causing the familiar delayed sunburn that arises 12-24 hours after exposure, skin aging, skin cancer (melanoma) and eye photokeratities. UVA acts indirectly with the skin by forming reactive oxygen species, causing an "immediate" sunburn that diminishes within 2 hours after exposure. UVA potentially plays a role in delayed sunburn and skin cancer. Although less energetic, UVA, which accounts for about 5.6% of sunlight, penetrates the skin more deeply, even into the dermis, than does UVB radiation, about 0.5% of sunlight, which generally is limited to the epidermis.

Melanoma has experienced the most rapid increase in the number of cases of all forms of cancer with more than 51,000 cases reported in America each year. As most cases have been attributed to sun exposure, the market for sunscreens presently exceeds $1 billion a year. Sunscreens are substances used to protect the skin by absorbing, reflecting and/or scattering damaging ultraviolet (UV) radiation. Sunscreens are typically used as a component in a cream or lotion. Sunscreen formulations are an article intended for the prevention of a disease and are regulated as an over-the counter (OTC) drug.

In a Final Monograph of May 21, 1999, entitled "Sunscreen Drug Products for Over-The-Counter Human Use" by the U.S. Food and Drug Administration (FDA), conditions were established under which OTC sunscreen drug products are generally recognized as safe and effective and not misbranded as part of FDA's ongoing review of OTC drug products. The Monograph established that an active ingredient of sunscreen products consists of any of the following (within the concentration specified for each ingredient when the finished product provides a minimum SPF value of not less than 2 as measured by a testing procedures established in the Monograph): Aminobenzoic acid (PABA) (15%); Avobenzone (3%); Cinoxate (3%); Dioxybenzone (3%); Homosalate (15%); Menthyl anthranilate (5%); Octocrylene (10%); Octyl methoxycinnamate (7.5%); Octyl salicylate (5%); Oxybenzone (6%); Padimate O (8%); Phenylbenzimidazole sulfonic acid (4%); Sulisobenzone (10%); Titanium dioxide (25%); Trolamine salicylate (12%); and Zinc oxide (25%). Since 1999 Ecamsule (10%) and Phenylbenzimidazole sulfonic acid (4%) have been approved for use as sunscreens. Also approved for use in Europe are: 4-Methylbenzylidene camphor (4%); Bisoctrizole (10%); Bemotrizinol (10%); Bisdisulizole disodium (10%); Drometrizole trisiloxane (15%); Benzophenone-9 (10%); Ethylhexyl triazone (5%); Diethylamino hydroxybenzoyl hexyl benzoate (10%); Iscotrizinol (10%); Polysilicone-15 (10%); and Isoamyl p-Methoxycinnamate (10%).

Of these sunscreens, only Polysilicone-15 is a silicon based polymeric sunscreen with the IUPAC name α-(trimethylsilyl)-ω-(trimethylsilyloxy)poly[oxy(dimethyl)silylene]-co-[oxy-(methyl)(2-{4-[2,2-bis(ethoxycarbonyl)vinyl]phenoxy}-1-methyleneethyl)silylene]-co-[oxy-(methyl)(2-(4-[2,2-bis(ethoxycarbonyevinyl]phenoxy)prop-1-enyl) silylene] with about 55 oxy(dimethyl)silylene units, about 4 oxy(methyl)(2-{4-[2,2-bis(ethoxycarbonyl)vinyl]phenoxy}-1-methyleneethyl) silylene units and about 1 oxy(methyl)(2-(4-[2,2-bis(ethoxycarbonyl)vinyl]phenoxy)prop-1-enyl)silylene units on average with an average molecular weight of 6,070. Statistically the random copolymer should have more than one percent of the chains that have no UV absorbing chromophores. An equivalent polymer of about 1,000 molecular weight would have less than half of the chains containing any UV absorbing chromophores. Polymeric sunscreens have the potential to provide a simple mode of distribution of the sunscreen in a vehicle, and reduce or eliminate absorption of the sunscreen by the skin to which it is applied. Many examples of polymeric sunscreens have been disclosed in the patent literature.

U.S. Pat. Nos. 7,291,322, 6,376,679, 6,312,673, 6,251,373, 6,221,343, 6,214,324, 6,200,557, 6,159,456, and 5,753,209, and U.S. Patent Application Publications 2007/0020204, 2004/0213746, 2002/0054860, and 2001/0026789 are directed to silicone based polymeric sunscreens that are random copolymers similar to Polysilicone-15 with various UV absorbing chromophores. Another form of polymeric sunscreens is random acrylic copolymers, as disclosed in U.S. Pat. Nos. 5,741,924, 5,487,885, 5,099,027 and 4,524,061 (which also discloses the polymers from a cyclic lactams). Substantive polymers are prepared by random vinyl copolymerization are disclosed in U.S. Pat. No. 7,087,692 and U.S. Patent Application Publication 2004/0101498 or by random condensation copolymerization, as disclosed in U.S. Pat. Nos. 4,004,074 and 3,864,473. Water dispersible polymeric sunscreens have been prepared by a random condensation copolymerization with polyethylene glycol monomers, as disclosed in U.S. Pat. Nos. 5,250,652, 5,243,021, and 5,134,223. An acrylamide homopolymer having UV active chromophores at every repeating unit is disclosed in U.S. Pat. No. 4,233,430. U.S. Patent Application Publication 2005/0186152 discloses a polyanhydride modified by the addition of nucleophilic UV active chromophores to place the chromophores on every repeating unit of the polymer chain with the formation of an equal amount of carboxylic acid groups on the polymer chain. U.S. Pat. Nos. 6,962,692, 6,926,887, 6,919,473, 6,899,866, 6,890,521, 6,800,274, and 5,993,789, disclose a homo-polyester sunscreen where UV active chromophores are on every repeating unit of the polymer.

As disclosed polymeric sunscreens have very high levels of UV absorbing chromophores that can result in a non-uniform distribution of the chromophores in the vehicles as in homopolymer or with random copolymers where molecular weights or UV absorbing chromophores are limited to those where a high molecular weights or high levels of UV absorbing units. Hence a polymeric system where the UV absorbing chromophore's distribution through out the polymer can be controlled with every polymer chain having the same proportion of UV absorbing chromophores independent of the molecular weight is attractive for a polymeric sunscreen.

BRIEF SUMMARY

Embodiments of the invention are directed to poly(non-conjugated diene) based sunscreens where the polymer has a plurality of one or more repeating units where each repeating unit has a chromophore unit having at least one UV absorbing chromophore situated between two mono-ene units. The mono-ene units of the polymer are separated from the chromophore unit by chains. In embodiments of the invention the chains can be a plurality of methylene units. The UV absorbing chromophores absorbs light in the UVA and/or UVB region of the electromagnetic spectrum. The UV absorbing chromophores can be equivalents to and derived from the conjugated group of the approved sunscreens: Aminobenzoic acid; Avobenzone; Cinoxate; Dioxybenzone; Homosalate; Menthyl anthranilate; Octocrylene; Octyl methoxycinnamate; Octyl salicylate; Oxybenzone; Padimate O; Phenylbenzimidazole sulfonic acid; Sulisobenzone; Trolamine salicylate; Ecamsule; Phenylbenzimidazole sulfonic acid; 4-Methylbenzylidene camphor; Bisoctrizole; Bemotrizinol; Bisdisulizole disodium; Drometrizole trisiloxane; Benzophenone-9; Ethylhexyl triazone; Diethylamino hydroxybenzoyl hexyl benzoate; Iscotrizinol; or Isoamyl p-Methoxycinnamate. The chromophore units can have bridging groups to connect the UV absorbing chromophores to the chromophore units. In embodiments of the invention, the bridging groups can include an alkylene group and a linking functionality that is a residue of an addition or a condensation reaction between functionality on the alkylene group and the UV absorbing chromophore.

Depending on the structures of the repeating units included in the poly(non-conjugated diene) based sunscreen, in some embodiments the UV absorbing chromophore can be periodically displaced along the backbone of the poly(non-conjugated diene). In other embodiments of the invention, the UV absorbing chromophore can be quasi-periodically or pseudo-randomly placed within the backbone of the poly(non-conjugated diene). In some embodiments of the invention, one or more functionality to impart: substantive properties; dispersivity; and/or an ability to specifically interact with particles or chemicals can be incorporated into at least one repeating unit, or can be attached at one or both terminal mono-enes of the poly(non-conjugated diene).

Other embodiments of the invention are directed to monomers for the preparation of the above poly(non-conjugated diene) based sunscreens. The monomers have two terminal ene units connected by a chain to a chromophore unit that has one or more UV absorbing chromophores that independently absorb light in the UVA and/or UVB regions of the electromagnetic spectrum. In one embodiment of the invention, the chains between the ene units and chromophore units of the monomers are of equal length and composition, which allows the formation of a periodic poly(non-conjugated diene). In another embodiment of the invention, the chains can be of different lengths and compositions in the same monomer to permit formation of a quasi-periodic poly(non-conjugated diene). The monomers can include functionality that can impart substantive properties, dispersivity, and/or an ability to specifically interact with particles or chemicals.

Other embodiments of the invention are directed to a method of preparing a poly(non-conjugated diene) based sunscreens where one or more of the above monomers are polymerized in the presence of a catalyst to promote acyclic olefin metathesis where ethylene is removed until a desired molecular weight is achieved. Olefin metathesis catalysts that can be used include Schrock's catalyst or Grub's catalyst.

Other embodiments of the invention are directed to sunscreen drug products where the poly(non-conjugated diene) based sunscreens are included with a vehicle. The vehicle can include a solvent for the poly(non-conjugated diene) or can include a combination of a non-solvent and a dispersing agent to emulsify or suspend the poly(non-conjugated diene) in the non-solvent vehicle.

Another embodiment of the invention is a method to prevent sunburn by providing a poly(non-conjugated diene) based sunscreen which is applied to skin. The poly(non-conjugated diene) based sunscreen can be provided as a component of a fluid that is a solution or a dispersion.

DETAILED DISCLOSURE

Figure 1A:
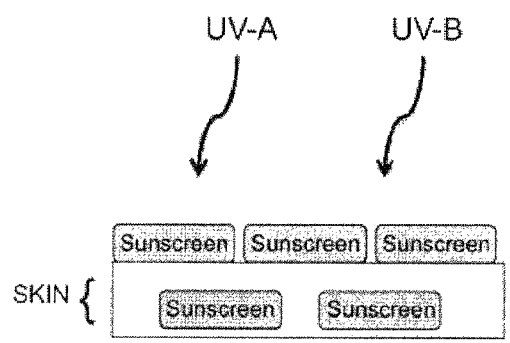
FIG. 1a shows a representation of current sunscreen technology and FIG. 1b shows a polymer having a unit that acts as a sunscreen according to embodiments of the invention.
Figure 1B:
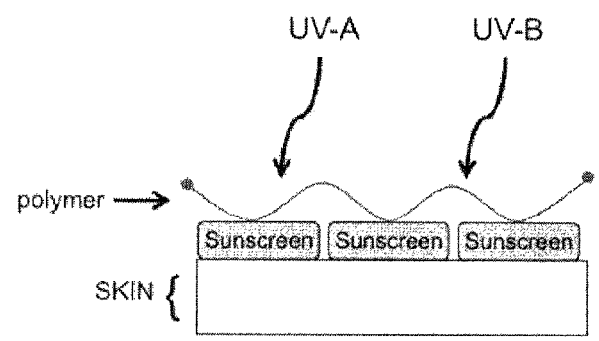
Figure 2A:
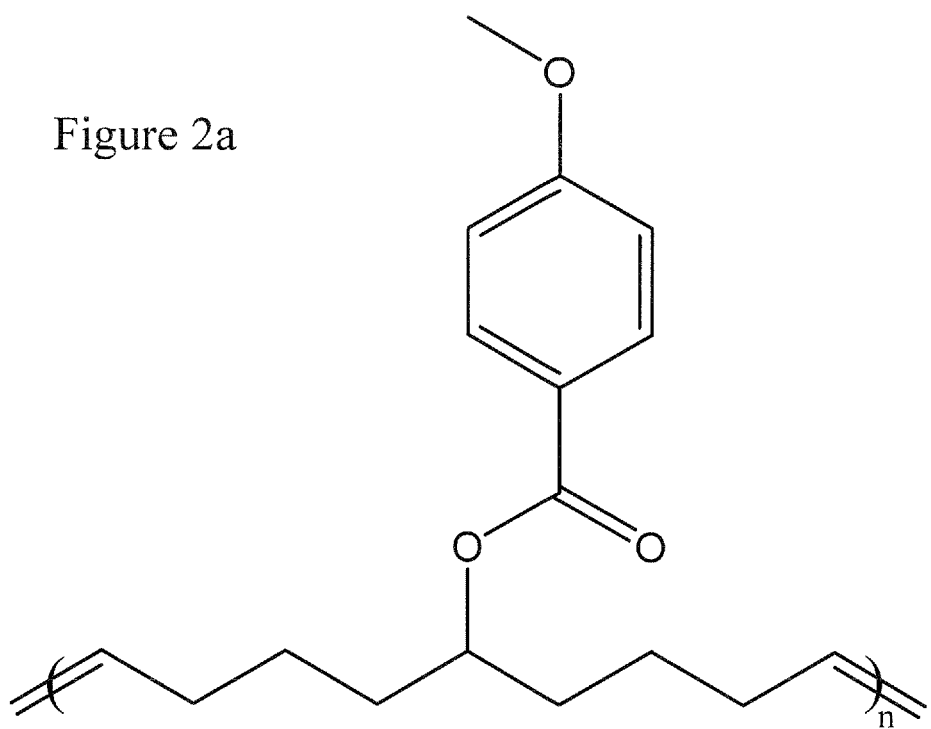
FIGS. 2a-2c show three poly(non-conjugated diene) based sunscreens with a UV absorbing chromophore on every ninth carbon along the backbone where the bridging group is: a) an ester; b) an amide; and c) an oligoether ester in accordance with embodiments of the invention.
Figure 2B:
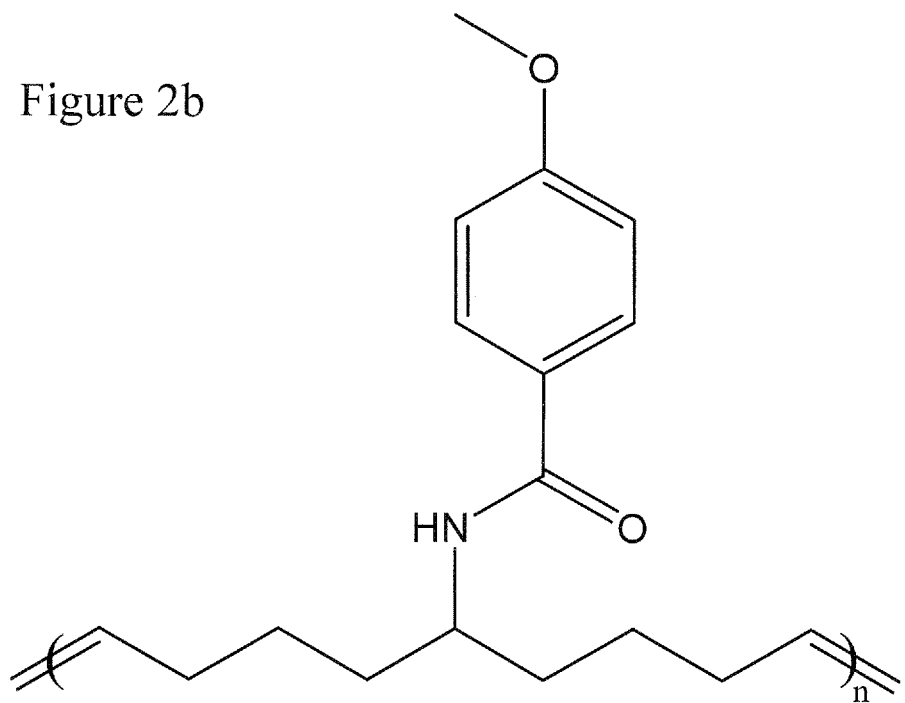
Figure 2C:
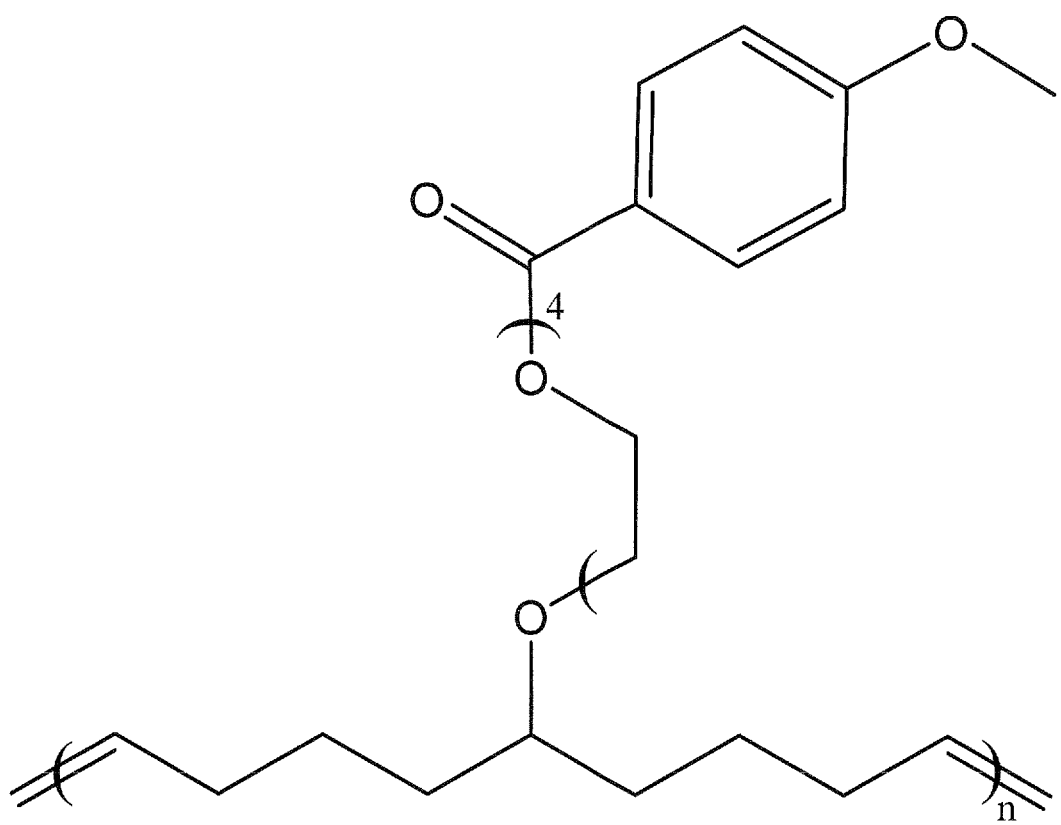

Embodiments of the invention are directed to poly(non-conjugated diene) based sunscreens that comprise polymers formed from α,ω-diene monomers covalently attached to chromophore units comprising one or more UV absorbing chromophores. As illustrated in FIG. 1, sunscreen molecules that are monomeric are often absorbable by the skin, which can allow radical/oxidative damage to the skin or can be toxic or carcinogenic to the sunscreen user. As also illustrated in FIG. 1, the polymeric structure will, in general, prohibit the absorption of the individual UV absorbing chromophores that function as the sunscreen. In one embodiment of the invention, a symmetric α,ω-diene monomer can be polymerized via a step-growth acyclic diene metathesis (ADMET) self-condensation polymerization to yield polymers with a perfectly defined primary structure where UV absorbing chromophores are equally spaced in a periodic fashion along the polymer backbone. Three poly(non-conjugated diene) based sunscreens according to embodiments of the invention are illustrated in FIG. 2. The monomer can be designed to have a chain with one specific chain length between the ene groups and a chromophore unit containing at least one UV absorbing chromophore.

In other embodiments of the invention, the UV absorbing chromophores can be separated from the enes by chains of two different lengths in a quasi periodic manner where there are only three different chain lengths between the UV absorbing chromophores. For example where a monomer with 5 methylene units situated between one mono-ene and the UV absorbing chromophore and 10 methylene units situated between the other mono-ene and the UV absorbing chromophore is polymerized, chains of 12, 17, and 22 carbons between UV absorbing chromophores in the polymer occur in a 1:2:1 ratio but where chains of 12 or 22 carbons cannot be on adjacent sides of any given UV absorbing chromophore. In yet another embodiment of the invention, a UV absorbing chromophores can be pseudo-randomly situated in a poly (non-conjugated diene) based sunscreen when two or more monomers are used where the chains between enes and. UV absorbing chromophores have three or more values. These systems are only pseudo-random because every repeating unit of the resulting copolymer has only specific lengths of chains between UV absorbing chromophores defined by the monomer feed ratio. For example, in similar manner to the quasi-periodic polymer above, two monomers, one having 5 methylene units between the UV absorbing chromophore and both mono-enes and another having 10 methylene units between the UV absorbing chromophore and both mono-ene units can be copolymerized in a one to one ratio to produces a polymer where chains of 12, 17, and 22 carbons between UV absorbing chromophores in a 1:2:1 ratio where chains of 12 or 22 carbons exist on adjacent sides of many UV absorbing chromophores of the copolymer.

In some embodiments of the invention, the chains between the terminal enes of the monomers and their UV absorbing chromophore unit can consist exclusively of methylene units. In other embodiments of the invention the chains can comprise units that provide specific groups that provide specific functionality to the resulting polymers. For example, the chains can have units that provide groups for substantive properties to the skin, groups to promote dispersion in a solvent, or groups to promote interaction with specific particles or chemicals in a sunscreen formulation. The structures of such groups are readily appreciated by those skilled in the art, and include, but are not exclusive to: tetra-alkyl ammonium salts, poly or oligo(ethyleneoxide) chains, or di or trialkoxysilane functionality. More than one UV absorbing chromophore can be attached to the monomer and two or more different UV absorbing chromophores can be included in the monomer. For example, one chromophore that absorbs UVA radiation and one chromophore that absorbs UVB radiation can be attached to the chromophore unit containing the UV absorbers.

The invention employs $\alpha,\omega$-diene monomers that can be homopolymerized by ADMET methods, yet, because the dienes are unreactive to a large proportion of chemical transformations, a large variety of transformations can be carried out to attach the UV absorbing chromophores or other groups to impart other properties for the polymers from these monomers. Although, in principle, all of the novel polymers can be prepared alternately by the ring-opening metathesis polymerization of cyclic mono-enes, typically the lengths of the chains between the ene units in the polymers are larger than those that generally permit efficient preparation of cyclic monoene monomers. By changing the number of methylene units between terminal mono-enes of the monomers and the chromophore unit, the resultant polymers can be loaded with different amounts of the UV absorbing chromophores. Where the repeating units are sufficiently large, the polymeric sunscreens can be oligomeric sunscreens as defined by the number of repeating units of the polymer, but can still be of sufficient molecular weight as to possess the desirable properties of polymeric sunscreens, such as a lack of toxicity or carcinogenicity. Because ADMET polymerization can be carried out to any degree and stopped when the desired amount of ethylene is generated, any desired molecular weight can be achieved.

In various embodiments of the invention, the molecular weight can be controlled by the inclusion of a mono-ene end-capper where the proportion of the diene monomers and the mono-enes can define the degree of polymerization of the resulting polymer in addition to the amount of ethylene released, or exclusively define the molecular weight for extremely high conversions of the terminal enes. The mono-enes can be compounds that have a group that provides substantive properties to the skin, groups to promote dispersion in a solvent or other vehicle, or promote interaction with specific particles or chemicals in a sunscreen formulation. The structures of such groups are readily appreciated by those skilled in the art, and include, but are not exclusive to: tetraalkyl ammonium salts, poly or oligo(ethyleneoxide) chains, or di or trialkoxysilane functionality.

The type of UV absorbing chromophores can be, but is not limited to those that have equivalent conjugated structures to those approved for use by the FDA or other worldwide regulatory agencies. Those approved chromophores are: Aminobenzoic acid; Avobenzone; Cinoxate; Dioxybenzone; Homosalate; Menthyl anthranilate; Octocrylene; Octyl methoxycinnamate; Octyl salicylate; Oxybenzone; Padimate O; Phenylbenzimidazole sulfonic acid; Sulisobenzone; Trolamine salicylate; Ecamsule; Phenylbenzimidazole sulfonic acid; 4-Methylbenzylidene camphor; Bisoctrizole; Bemotrizinol; Bisdisulizole disodium; Drometrizole trisiloxane; Benzophenone-9; Ethylhexyl triazone; Diethylamino hydroxybenzoyl hexyl benzoate; Iscotrizinol; Isoamyl p-Methoxycinnamate; and those attached to Polysilicone-15. Other UV absorbing chromophores can be used including those equivalent to UV absorbing conjugated systems disclosed in: U.S. Pat. Nos. 7,291,322; 7,087,692; 6,962,692; 6,926,887; 6,919,473; 6,899,866; 6,890,521; 6,800,274; 6,376,679; 6,312,673; 6,251,373; 6,221,343; 6,214,324; 6,200,557; 6,159,456; 5,993,789; 5,753,209; 5,741,924; 5,487,885; 5,250,652; 5,243,021; 5,134,223; 5,099,027; 4,524,061; 4,233,430; 4,004,074; and 3,864,473 and U.S. Patent Application Publications 2007/0020204; 2005/0186152; 2004/0213746; 2004/0101498; 2002/0054860; and 2001/0026789. Many other conjugated systems that absorb in the UVA and/or UVB spectral ranges can be used, even some that are known to be damaging to the skin or to other organs or systems of an individual using a sunscreen, because the chromophores is irreversibly bound to a polymer chain, rendering it passive to the system. The UV absorbing chromophores can be linked in the chromophore unit by any sufficiently stable bridging group. For example, where the conjugated UV absorbing chromophore unit contains a carboxylic acid group, the chromophore unit can have a hydroxy group and the UV absorbing chromophores can be attached via ester functionality. One skilled in the art can readily appreciate appropriate complimentary functionalities to bridge the UV absorbing chromophores to chromophore unit of the monomers. Some embodiments of the invention are directed to preparation of monomers for the preparation of the novel poly(non-conjugated diene) based sunscreens where a UV absorbing chromophore comprising molecule is attached to a functional group of an $\alpha,\omega$-diene molecule.

Figure 3:
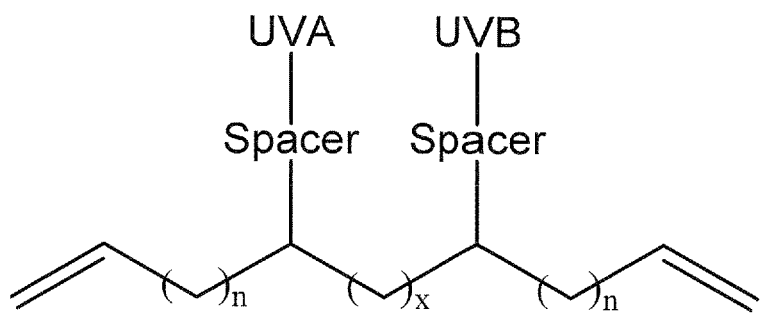
FIG. 3 shows a monomer for preparing a poly(non-conjugated diene) based sunscreen that has a chromophore unit that is a 5 to 10 carbon unit with two different UV absorbing chromophores attached at the ends of the carbon by a spacer group.
Figure 4:
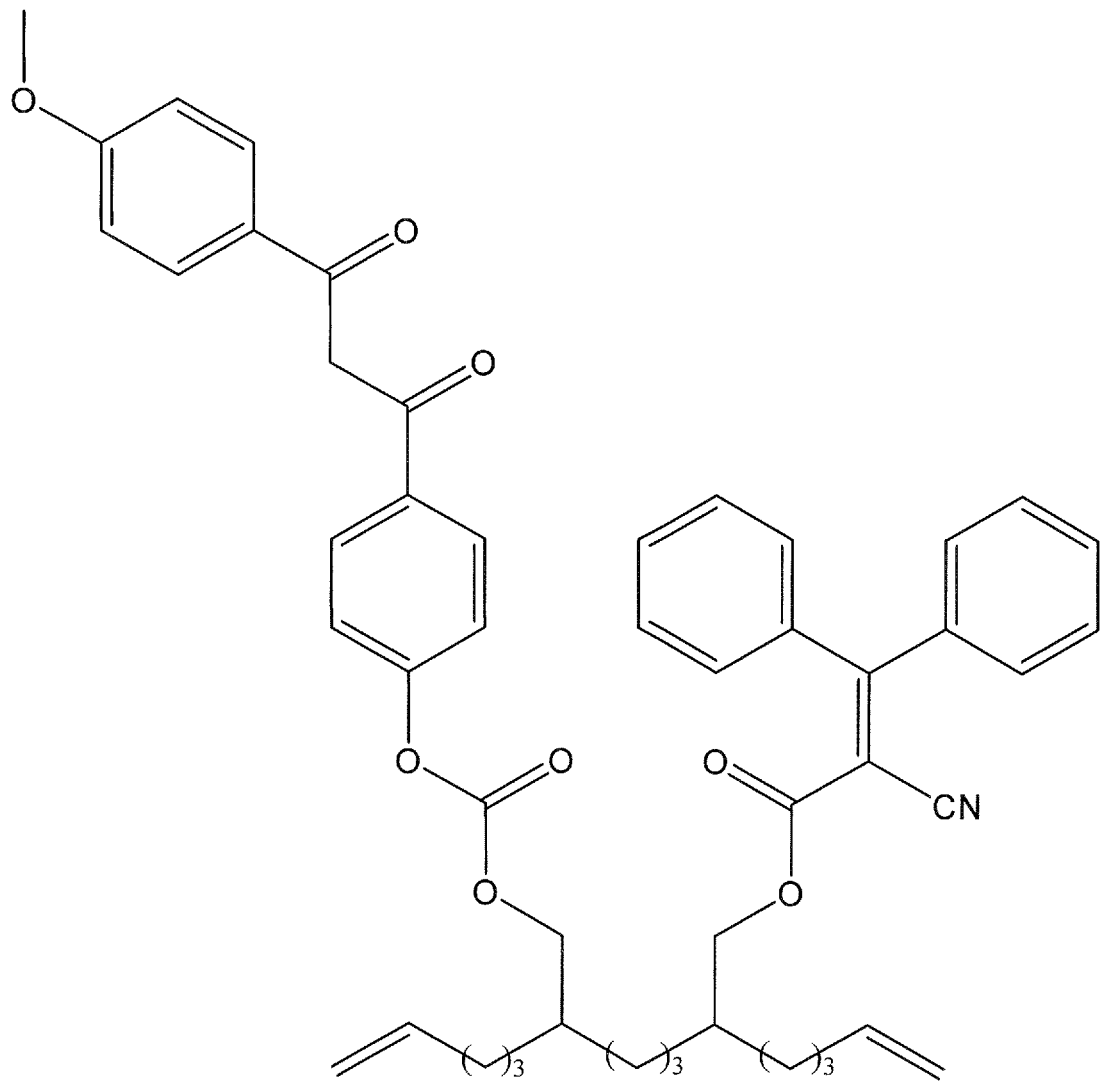
FIG. 4 shows a specific monomer according to that illustrated in FIG. 3 where the UV absorbing chromophores are derived from Avobenzone and Octocrylene type of sunscreen components and connected to a 5 carbon chromophore unit where one bridging group is a methylene spacer with a carbonate functional group and the other bridging group is a methylene spacer with an ester functional group.

The chromophore unit comprising the UV absorbing chromophore or chromophores can include a coupling unit between a plurality of UV absorbing chromophores. For example, as illustrated in FIG. 3, a chromophore unit can have a UVA absorbing chromophore and a UVB absorbing chromophore attached at the ends of a 5 to 10 carbon linked chromophore unit by a spacer.

Figure 5:
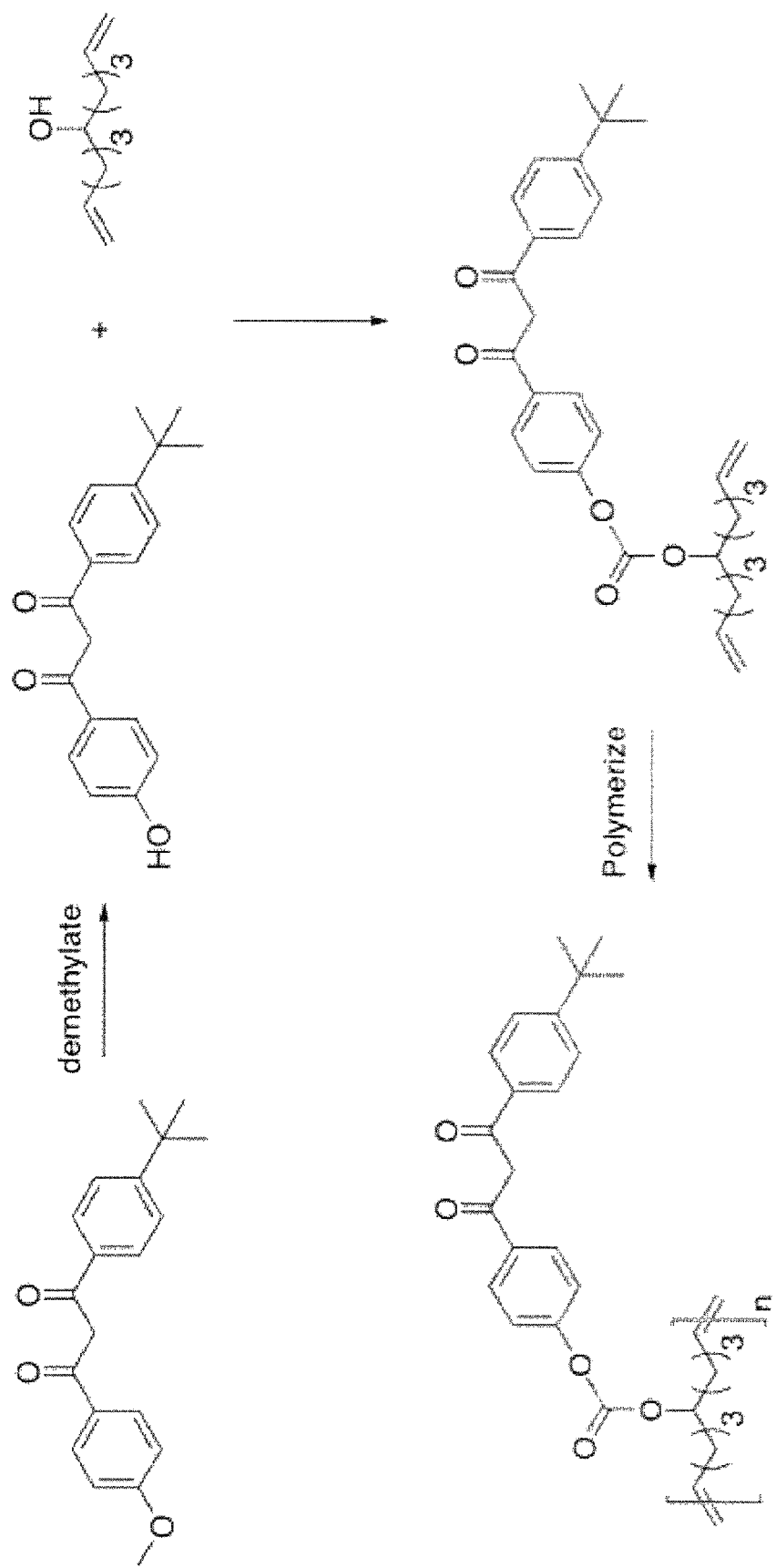
FIG. 5 shows the synthesis of a monomer and its polymerization to a poly(non-conjugated diene) based sunscreen in accordance with embodiments of the invention.

Embodiments of the invention are directed to the formation of poly(non-conjugated diene) based sunscreens by the ADMET polymerization of α,ω-diene monomers covalently attached to UV absorbing chromophores. Monomers, as described above, can be coupled by the use of any known metathesis catalyst, for example Schrock's catalyst Mo(=CHCMe$_2$Ph)(N-2,6-C$_6$H$_3$-i-Pr$_2$)(OCMe(CF$_3$)$_2$)$_2$ or Grubbs' catalyst RuCl$_2$(=CHPh)(PCy$_3$)$_2$. The formation of an α,ω-diene monomers and its polymerization to a poly (non-conjugated diene) based sunscreen is illustrated by example in FIG. 5 for a polymer formed having the UV absorbing chromophore derived from Avobenzone.

In some embodiments of the invention, the poly(non-conjugated diene) based sunscreens can be further modified at the residual ene units of the polymer backbone. The ene units can be hydrogenated to methylene units or can undergo other addition reactions to form functional groups that can be further elaborated into other groups. For example, water, ammonia, hydrogen sulphide, or HCl can be added across the ene units to form hydroxy, amine, thiol or chloride units with some regularity along the polymer backbone. The resulting units can be used to undergo condensation or addition reactions to form other functional groups. For example, a hydroxy unit can be used to add to ethylene oxide or other epoxy group or to condense with a carboxylic acid ester or halide to functionalize the polymer. Some or all of the ene units can be converted. Those skilled in the art can readily envision the scope of possible structures that can be generated from the ene units.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

We claim:

1. A poly(non-conjugated diene) based sunscreen comprising a polymer comprising a plurality of at least one repeating unit that comprises at least one chromophore unit situated between two mono-ene units, wherein said chromophore unit comprises a UV absorbing chromophore, and wherein each of said mono-ene units and said chromophore unit are connected by chains, wherein said UV absorbing chromophore absorbs light in the UVA and/or UVB region of the electromagnetic spectrum.

2. The sunscreen of claim 1, wherein said UV absorbing chromophore comprises a conjugated group derived from Aminobenzoic acid, Avobenzone, Cinoxate, Dioxybenzone, Homosalate, Menthyl anthranilate, Octocrylene, Octyl methoxycinnamate, Octyl salicylate, Oxybenzone, Padimate O, Phenylbenzimidazole sulfonic acid, Sulisobenzone, Trolamine salicylate, Ecamsule, Methylbenzylidene camphor, Bisoctrizole, Bemotrizinol, Bisdisulizole disodium, Drometrizole trisiloxane, Benzophenone-9, Ethylhexyl triazone, Diethylamino hydroxybenzoyl hexyl benzoate, Iscotrizinol, or Isoamyl p-Methoxycinnamate.

3. The sunscreen of claim 1, wherein said chains comprise a plurality of methylene units.

4. The sunscreen of claim 1, wherein said chromophore unit comprises said UV absorbing chromophore and a bridging group.

5. The sunscreen of claim 4, wherein said bridging group comprises an alkylene group and a linking functionality, wherein said linking functionality comprises a residue of an addition or a condensation reaction between functionality on said alkylene group and said UV absorbing chromophore.

6. The sunscreen of claim 1, wherein said UV absorbing chromophores are periodically, quasi-periodically, or pseudo-randomly placed along the chain of said poly(non-conjugated diene) based sunscreen.

7. A monomer for preparation of a poly(non-conjugated diene) based sunscreens according to claim 1, comprising two terminal ene units and a chromophore unit that comprises at least one UV absorbing chromophore, wherein said chromophore unit is connected by chains to said terminal ene units, wherein said UV absorbing chromophore absorbs light in the UVA and/or UVB region of the electromagnetic spectrum.

8. The monomer of claim 7, wherein said UV absorbing chromophore comprises a conjugated group derived from Aminobenzoic acid, Avobenzone, Cinoxate, Dioxybenzone, Homosalate, Menthyl anthranilate, Octocrylene, Octyl methoxycinnamate, Octyl salicylate, Oxybenzone, Padimate O, Phenylbenzimidazole sulfonic acid, Sulisobenzone, Trolamine salicylate, Ecamsule, Methylbenzylidene camphor, Bisoctrizole, Bemotrizinol, Bisdisulizole disodium, Drometrizole trisiloxane, Benzophenone-9, Ethylhexyl triazone, Diethylamino hydroxybenzoyl hexyl benzoate, Iscotrizinol, or Isoamyl p-Methoxycinnamate.

9. The monomer of claim 7, wherein said chains comprise a plurality of methylene units.

10. The monomer of claim 7, wherein said chromophore unit comprising said UV absorbing chromophore comprises said UV absorbing unit and a bridging group.

11. The monomer of claim 10, wherein said bridging group comprises an alkylene group and a linking functionality, wherein said linking functionality comprises a residue of an addition or a condensation reaction between functional groups of said alkylene group and said UV absorbing chromophore.

12. The monomer of claim 7, wherein said chains are of equal length or are of different lengths and said chains are of the same or different composition.

13. A method of preparing a poly(non-conjugated diene) based sunscreen according to claim 1, comprising:
providing a plurality of at least one monomer comprising two terminal ene units and a chromophore unit that comprises at least one UV absorbing chromophore, wherein said chromophore unit and said terminal ene units are connected by chains, and wherein said at least one UV absorbing chromophore independently absorbs light in the UVA and/or UVB region of the electromagnetic spectrum;
providing a catalyst to promote acyclic olefin metathesis;
combining said catalyst with said monomers; and
removing ethylene until a desired molecular weight is achieved.

14. The method of claim 13, wherein said catalyst comprises Schrock's catalyst or Grub's catalyst.

15. A sunscreen drug product, comprising a poly(non-conjugated diene) according to claim 1, wherein said at least one UV absorbing chromophore independently absorbs light in the UVA and/or UVB region of the electromagnetic spectrum and a vehicle.

16. The sunscreen drug product of claim 15, wherein said vehicle comprises: a solvent for said poly(non-conjugated diene); a non-solvent for said poly(non-conjugated diene) and a dispersing agent; or any combination thereof.

17. A method to prevent sunburn comprising the steps of:
providing a poly(non-conjugated diene) based sunscreen according to claim 1; and applying said poly(non-conjugated diene) based sunscreen to skin, wherein, optionally, said poly(non-conjugated diene) based sunscreen is provided as a component of a fluid comprising a solution or a dispersion.

* * * * *

UNITED STATES PATENT AND TRADEMARK OFFICE
CERTIFICATE OF CORRECTION

PATENT NO. : 8,540,976 B2  Page 1 of 1
APPLICATION NO. : 13/257775
DATED : September 24, 2013
INVENTOR(S) : James Klein Leonard et al.

It is certified that error appears in the above-identified patent and that said Letters Patent is hereby corrected as shown below:

In the Specifications

Column 2,
Line 9, "(ethoxycaronyevinyl]" should read --(ethoxycarbonyl)vinyl]--.

In the Claims

Column 7,
Line 55, "Methylbenzylidene camphor" should read --4-Methylbenzylidene camphor--.

Column 8,
Line 21, "Methylbenzylidene camphor" should read --4-Methylbenzylidene camphor--.

Signed and Sealed this
Twenty-fifth Day of March, 2014

Michelle K. Lee
*Deputy Director of the United States Patent and Trademark Office*